United States Patent
Ahonen

Patent Number: 6,123,188
Date of Patent: Sep. 26, 2000

[54] STORAGE CONTAINER THAT ISOLATES AND CONTAINS CONTAMINATED MEDICAL EQUIPMENT INCLUDING A RACK FOR CARRYING MEDICAL INSTRUMENTS INTO AND OUT OF THE OPERATING ROOM

[76] Inventor: Peggy Susan Ahonen, 1406 Bauman, Royal Oak, Mich. 48073-2004

[21] Appl. No.: 09/134,886

[22] Filed: Aug. 15, 1998

[51] Int. Cl.[7] .................................................. B65D 81/18
[52] U.S. Cl. .......................... 206/210; 206/365; 206/366; 206/370
[58] Field of Search .................................. 206/63.5, 210, 206/366, 365, 370; 422/297, 300

[56] References Cited

U.S. PATENT DOCUMENTS

| | | | |
|---|---|---|---|
| 1,816,425 | 7/1931 | Everett et al. | 422/297 |
| 4,779,728 | 10/1988 | Hanifl et al. | 206/63.5 |
| 4,959,220 | 9/1990 | Yamamoto . | |
| 5,038,929 | 8/1991 | Kubofcik . | |
| 5,152,814 | 10/1992 | Nelson . | |
| 5,161,681 | 11/1992 | Kemp et al. | 206/210 |
| 5,172,808 | 12/1992 | Bruno . | |
| 5,190,879 | 3/1993 | Wolfe . | |
| 5,225,160 | 7/1993 | Sanford . | |
| 5,230,427 | 7/1993 | Betts et al. | 206/347 |
| 5,259,501 | 11/1993 | Withers et al. | 206/366 |
| 5,291,997 | 3/1994 | He et al. | 206/366 |
| 5,300,752 | 4/1994 | Elmerick . | |
| 5,323,902 | 6/1994 | Palmer et al. | 206/366 |
| 5,372,252 | 12/1994 | Alexander | 206/366 |
| 5,385,105 | 1/1995 | Withers . | |
| 5,424,265 | 6/1995 | Weinstein | 210/282 |
| 5,495,941 | 3/1996 | Leonard | 206/366 |
| 5,531,341 | 7/1996 | Shlisky | 206/366 |
| 5,584,386 | 12/1996 | Ahonen . | |
| 5,667,564 | 9/1997 | Weinberg . | |
| 5,823,340 | 10/1998 | Maihofer | 206/370 |
| 5,823,363 | 10/1998 | Cassel | 206/366 |

*Primary Examiner*—Paul T. Sewell
*Assistant Examiner*—J. Mohandesi

[57] ABSTRACT

A storage container for holding and disinfecting invasive medical instruments, such as hypodermic needles and scalpels. The storage container is elongated and in a tubular configuration, having a closed lower end and an open upper end. The storage container is made of puncture resistant, gas autoclavable material. A plastic twist off lid is attached to the open upper end and including a string connected between the lid and container to attach the lid to the container. A port hole of entry connected thereto near the open upper end, said port hole of entry comprising a second container section of smaller cross section than the cross section of the storage container and connected thereto in sealed fashion to allow entry of solution or chemicals to the container without opening the lid on the container upper end. The storage container having a mouth rim to block and prevent a back splash of airborne microorganism from the container. The disinfecting fluid in the storage container kills various viruses and germs, and a base container holds the storage container securely.

7 Claims, 4 Drawing Sheets

STORAGE CONTAINER THAT ISOLATES AND CONTAINS CONTAMINATED MEDICAL EQUIPMENT INCLUDING A RACK FOR CARRYING MEDICAL INSTRUMENTS INTO AND OUT OF THE OPERATING ROOM

BACKGROUND OF THE INVENTION

1. Field of the Invention

This invention relates generally to a container that allow for the immediate isolation and containment of contaminated medical instruments and used medical devices. The medical equipment including such things as used scalpels, needles, syringes, trachs, suction caths, IV's, used bandages, and G tube feeding tubes, foley caths, or any medical equipment that is contaminated with biohazardous waste. The contaminated medical equipment is simply put in the container, and the airtight lid is sealed; all reuseable equipment medical equipment is disinfected prior to the lid of the container being reopened. Due to the containers simple cost effective design, and its airtight sealing lid and sterile hollow antechamber; the container can function to store, hold, and safely, transfer any medical equipment, devices, human tissues, or implants materials; that must maintain sterility.

Due to the containers design and multiple functions it can preform, any type of wetting, soaking, disinfectant, chemical, medicine, or preservative; can be safely be added to meet the exact needs of the function being preformed, by the container.

2. Discussion of the Related Art

Worldwide in the health care environment there is a crisis due to Nosocomial Infections (hospital acquired infections). In the United States alone current spending to treat Nosocomial Infections is approximately $3 billion dollars annually; or a breakdown of $3500.00 per infection. Worldwide the problem with drug resistant microorganisms have not only increased the cost of treatment, but has also made the treatment of these infections more difficult. Nosocomial Infections on the human level, cause patient suffering and sometimes death.

Millions of dollars of medical research and clinical studies have demonstrated the high level of patient venerability to harmful microorganisms in the hospital environment. I have developed a theory of isolation to support the needed use of my device to help isolate and contain harmful microorganisms. The theory of isolation simply is to reduce the overall load or volume of microorganisms that are disease causing by isolating and containing them; thereby reduces the risk of disease transmission, in an environment such as a hospital. Thereby using the device will protect the patients to some degree. The primary function of the container will be to allow for the immediate isolation of biological contaminates at their human portal of exit sites, (in other words, isolates them where they are excreted). This isolation should help to reduce the overall microbial load and colony forming units in the air of the hospital environment. Therefore, the theory of isolation and the use of the container have the potential to reduce the overall rate of Nosocomial Infections worldwide. Due to the containers simple design, which is cost effective, and easy to use, the container will be capable of performing many functions. Basically the container can hold, store, or transfer any medical equipment, under strict sterile conditions. Or again the container can be used to isolate contaminated medical equipment, and disinfect all reusable equipment prior to opening the lid of the sealed container.

For operating room purposes the container is placed on a rack that allows for the holding of multiple containers. Although any type of rack or housing unit can be used, the preferred housing unit allows for the surgical team to have visual access of exactly where each instrument is located on the lid of the housing unit. The housing unit will vary in size, depending on what type of surgery equipment it is holding. The used instruments can be returned to the same container and the disinfectant is added in the operating room; and /or the new container can be used with the disinfectant already in the container. The racks can be numbered to make sure that all instruments have been accounted for.

3. Discussion of Prior Art

Many types of containers are known in the prior art that are used to temporarily store hypodermic needles and the like, including disinfecting them since the onset of the Aids virus. Both U.S. patents of Bruno (U.S. Pat. No. 5,172,808) and Kubofcik (U.S. Pat. No. 5,038,929) have been analyzed; since they are both elongated shaped containers to temporarily hold and store contaminated hypodermic needles. The Bruno patent also sites the use of magnets to secure the container, along with an elongated shape of container. Both the Bruno and Kubofcik are designed to function as and only as safe storage container to hold contaminated needles. Both patents are not designed to seal airtight so that they can prevent the spread of airborne germs; or transfer sterile equipment in a hollow sterile inter-chamber. In this analysis both the Bruno and Kubofcik patents were not intended to be used to isolate and contain medical waste contaminated with airborne germs. These patents both were simply designed to protect health care workers from contaminated needle puncture wounds.

SUMMARY OF THE INVENTION

In accordance with the teaching of the present invention, a container to isolate and contain contaminated medical equipment; including a rack for carrying medical instruments into and out of the operating room. As illustrated in the accompanying drawings, an elongated storage container, preferably in a tubular configuration, having a closed lower end and an open upper end, for storing sterilized medical instruments for the transportation of the instruments, to protect the instruments from airborne germs and storing and disinfecting the medical instruments used in the operating room, prior to the containers being reopened again in the supply room. The container can come in any shape or design for any type of medical instrument or device. A twist of lid, or other suitable lid, is preferred provided that it seals the container to form an airtight seal. The lid can include the universal biohazard waste symbol. A string, or any other material can attach the lid to the container, to allow for easy sealing, and to prevent the lid from falling on the floor or getting lost. The container is made of a plastic material, both puncture resistant and gas autoclavable, although any other type of material could be used. The plastic is molded to include a port hole of entry or stem to allow water or any other chemical or medical solution to safely be put in the container. The port hole can include a semipermeable membrane and/or twist off lid or other lid that seals air tight, to prevent the possibility of air leakage of liquid leakage from the container.

When the container is being used to isolate and contain serious airborne diseases the container can be designed to include a mouth rim at the opening of the container to help prevent a back splash of germs when the contaminated instrument is inserted. This mouth rim can be made of rubber or plastic suitable material that is autoclavable. It can be designed to have absorbing material fibers that can be pre-chemically treated to help kill certain microorganism. The port hole of entry could be used to inflate the mouth rim, and allow for a safe method of irrigation of the absorbing fibers; with the disinfecting medium. The mouth rim must be tested in FDA pretesting to determine if it is effective enough to merit its added cost; again this feature is only for very serious airborne microorganisms. With this design the container may require a second port hole to be added to allow the disinfectant to be added or activated.

In some of the embodiments, the plastic that makes the containers or the lids, may be color coded to provide warnings of the contents, function of the container, or level of biohazardous waste. The containers or lids can be designed to indicate a color code for each disease, or be microorganism specific, or indicate if the contents of the container are reusable medical equipment or disposable waste. Color codes can be assigned for each function of the container, or for any reason that constitutes a safer environment for the patients or staff of hospitals worldwide.

The disinfecting materials or solutions can be put into the containers for disinfecting the used medical equipment. It is possible that they may be prepackaged and ready to use. In one embodiment, the disinfecting material is a mixture is a mixture that includes Calcium Hypochlorite Dihydrate and heat treated Sodium Bicarbonate. Although any type chemical, medicine, solution, preservative, or disinfectant may be used or stored in the container. By mixing these two chemicals with water, an effervescent actions occurs, which is necessary to help remove all organic waste off of the reusable equipment. Of course any other suitable mixture of a disinfectant and a effervescent can be used that provides this type of effervescense as long as they are chemically compatible, and will work together, and will not tarnish the equipment.

The water, or chemical is simply added to the container via the port hole of entry to activate the chemical process. The disinfectant used, may be chemically designed to be organism specific, since bleach only kills most microorganisms; and will not kill all microorganisms. Since the container has multiple medical functions, many different chemical medicines, solutions. Or preservatives; may be stored or added via the port hole of entry. If and when possible water will be the preferred solution to chemically activate the formulas; for the protection of the patients and health care workers worldwide. The chemical may be prepackaged, or ready to use in plastic squeeze the top off bottles or syringes, simply for the convenience of the health care workers. The chemicals in what ever for prepackaged may be stored in the containers and removed prior to use.

A plastic or metal rack is provided to hold the container. The container is specially configured so that it can be secured to the rack. The rack is designed to be reusable and resterilizable. The container is placed on the rack at a 15, 30, 45, 60, 75, 90, or 120 decree angle to allow for easy insertion of the contaminated object. A metal or plastic clamping device can be used to hold the top of the container in place in the rack. A magnet and magnetic tape can be used to adhere to the bottle of the container so that the containers are secured in the rack; or any adhering materials can be used such as velcro. The rack can be heavy enough to prevent any movement or shifting of the rack. A large rack or housing unit can be provided to hold a plurality of containers for such situations as in an operating room.

For the operating room the rack or housing unit is made of a gas autoclavable plastic or surgeon steel materials. The lid of the housing unit is totally removable or opens individually over each container. The lid allows for the surgical team to have exact visual knowledge where each instrument is housed in the unit. This method of visual access, may be accomplished by symbols, pictures, letters, or anything that the surgical team can identify with easily. The used equipment can be put in the same container (and the chemicals can be added manually, which will save on cost for poor nations), or a completely new container can be used with the disinfectant prepackaged or stored in the container. The used equipment may be returned to the same rack or housing unit and/or another rack may be used. The rack or housing unit must be numbered to allow the surgical team to account for all instrumentation and sponges used. The housing unit itself may provide a numberial grid.

The container and housing unit provide safe storage area for hypodermic needles and contaminated medical instruments. (IV caths, foley cath, lab sticks, tracheostomy tubes, and other medical equipment). The container can be designed to house any type of tubing or bio-waste excreted by any type of vacuum, suction, or pumping equipment; or any type of equipment developed in the future that excretes a high level of biocontaminates. In this manner, all of the contaminated instruments can be put into a secure container and be disposed of at a reasonable cost; or safely reopened after the equipment has been disinfected.

BRIEF DESCRIPTION OF THE DRAWINGS

FIG. 1. Top view of the storage housing units visual access lid.

FIG. 2. Side view of housing units visual access lid.

FIG. 3. Frontal view of housing units visual access lid.

FIG. 4. All views of storage container to isolate and contain, contaminated medical equipment; and transfer medical equipment, into and out of the operating room, including a rack.

DETAILED DESCRIPTION OF THE PREFERRED EMBODIMENTS

The following description of the preferred embodiments directed to a storage container to isolate and contain contaminated medical equipment; including a rack for carrying medical instruments into and out of the operating room; is merely exemplary in nature and is in no way intended to limit the invention or its applications or uses.

FIGS. 1–3 show various views of container 80, a housing unit that is designed to hold storage container 33, in plurality, lid 11 of container 80, allows for visual access to the exact location of each instrument. Lid 11 can open fully or lid 1 can open individually over each instrument, housed in container 80. Side wall 2 of container 80 is made of gas autoclavable plastic or surgeon steel, which is the preferred material. The lid 11, can be made of the same material, or of a different material of container 80, although both are preferred to be made out of surgeon steel, and lids both 1 and 11 will have engraved into the surgeons steel all numbers and letters required to allow the surgical team visual access. The writing 4 or words can be provided to help provide visual access of lid 11, relaying the knowledge of where each exact instrument is located in container 80. Individual lid opening groove 5, allows for lid 1 to be easily opened; to allow the surgical nurse to easily remove storage container 33, out of container 80. Numbers 6 on lid 11 can assist the surgical team in allowing for a easy pre-surgery set up, also to give the total count off used instruments and sponges, and total number of instruments sent into any given surgery (inventory).

The engraving of all words 4 and numbers 6, take in consideration of the world market of lid 11, and container 80, and the magnitude of the different languages and different types of surgical procedures that will each require their own designed lid 11, and container 80 will have to vary in shape and size to allow for different size equipment.

DETAILED DESCRIPTION OF THE PREFERRED EMBODIMENTS

Figure 1:
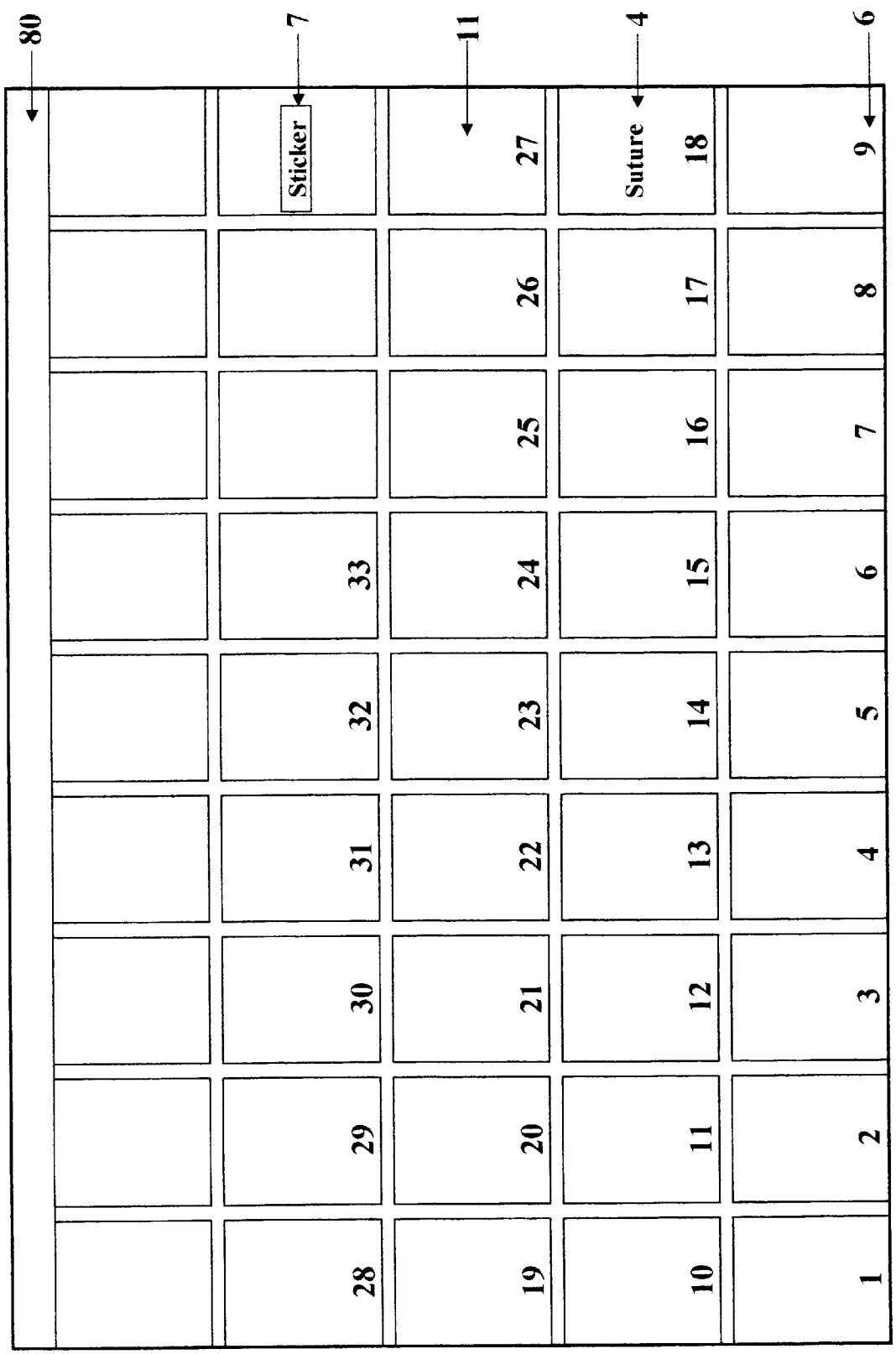
Figure 2:
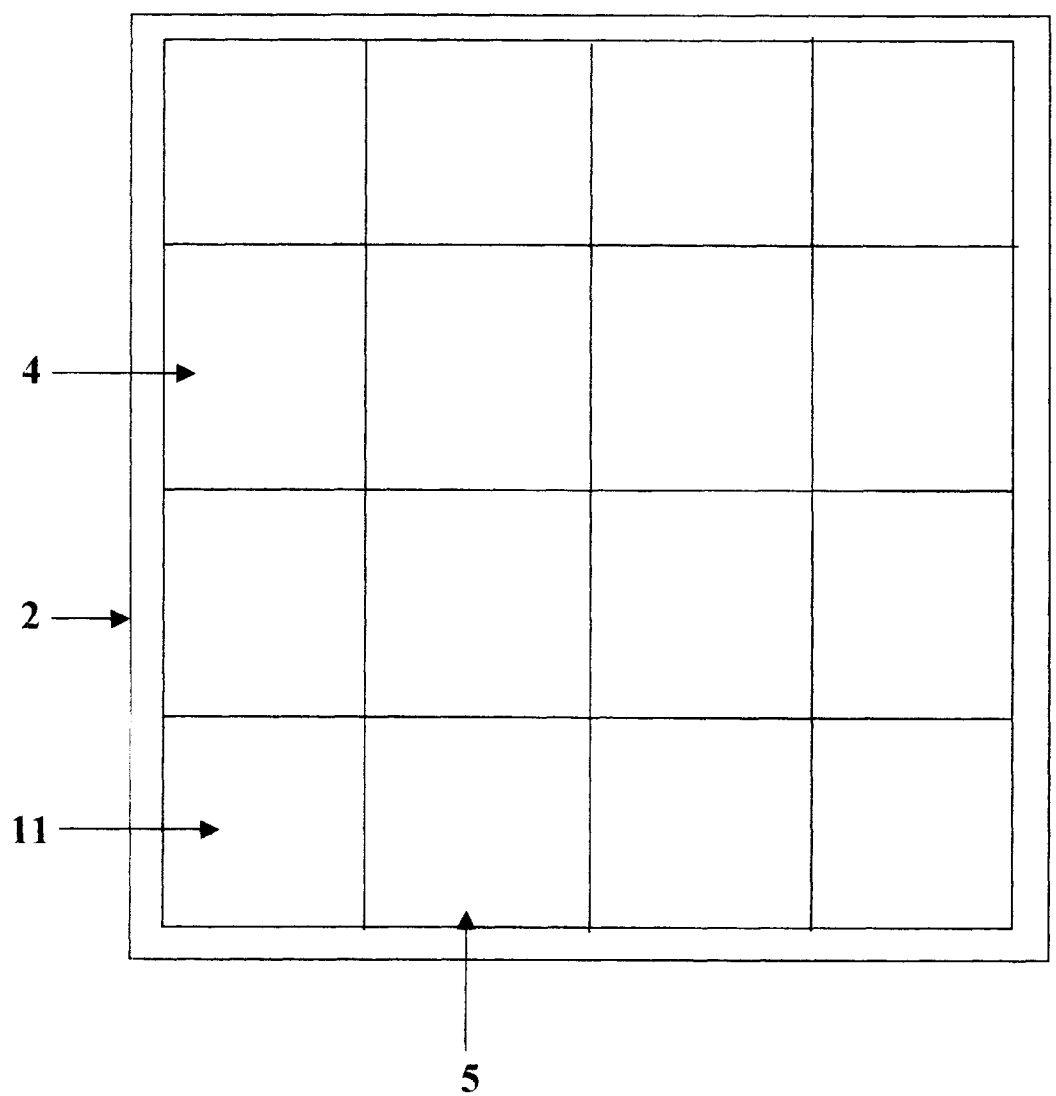
Figure 3:
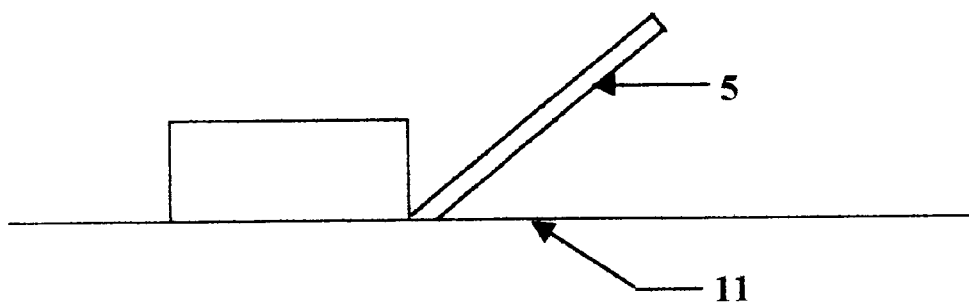
Figure 4:
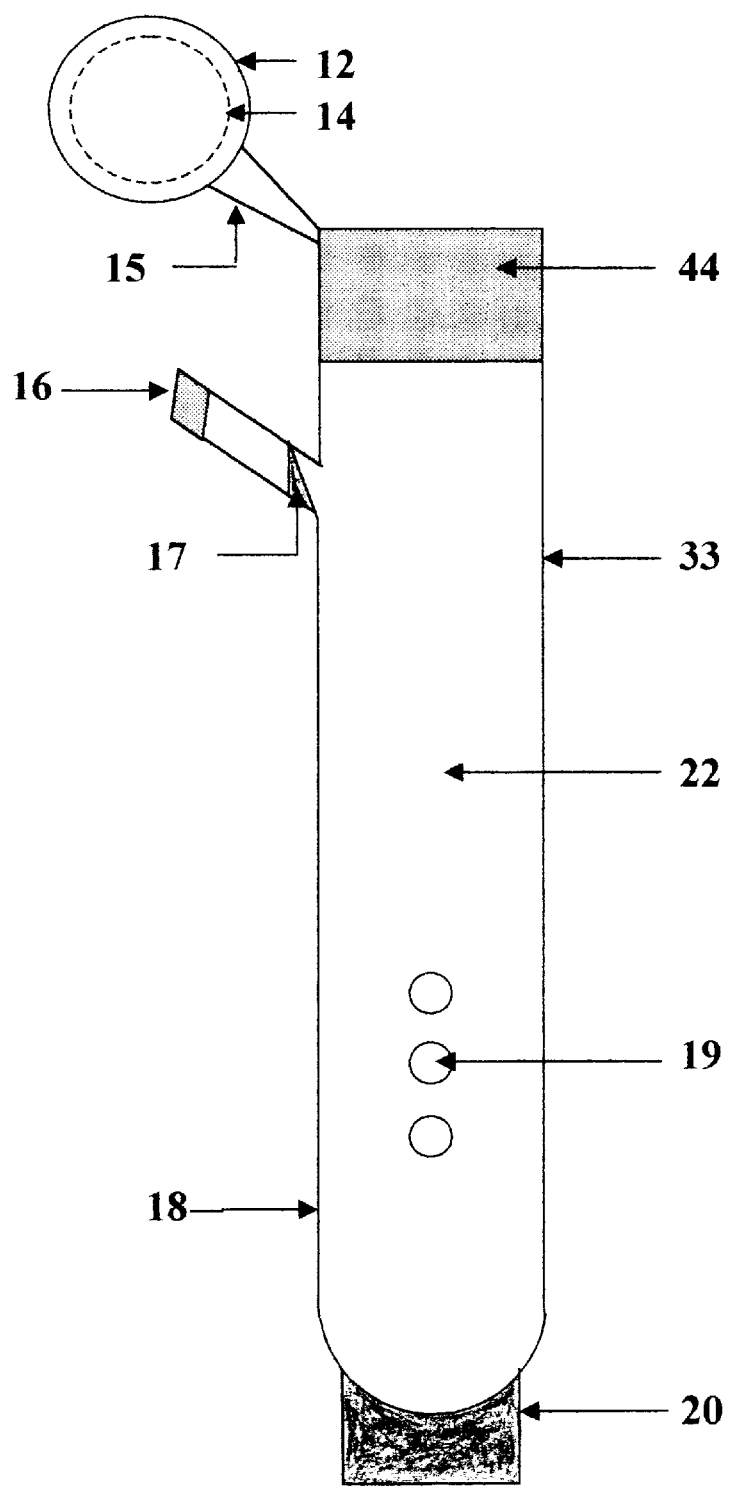

Container 33, and elongated tubular shaped embodiment, having a closed bottom, And a open upper end, made out of a cost effective plastic, that is gas autoclavable, And puncture resistant. Plastic twist off lid 12, forms a perfect airtight seal, when It seal container 33. Universal symbol of biohazards waste 14, warns patients and Visitors not to open container 33. Connector string 15, made of easy cheap material Connects the lids to container 33, to prevent the lids from being lost, or falling on the Floor. Sticker 7, can label container 33, or housing unit 80, with numbers such as 10, on container 33; number 10 will give the surgical the location to put container 33, in housing unit 80. Port hole of entry 16, allows the solution or chemical, or chemical activate to be added safely in to container 33. The semipermeable membrane 17, of allows the solution to be added to the container 33, without a backslash of chemical or germs leaking. Color codes 18, may be added to container 33, exterior for many medical reasons, that indicate content or usage. Dry chemicals 19, for disinfecting, wetting, soaking, preservative, or to assist in the removal of organic waste, medicating, or any other medical function. Magnets 20, or any other adhering material such as Velcro, can be used to prevent any moving or shifting on container 33, when it is used with a base. Sterile hollow interchamber 22, provides a maintained sterile field space for transporting Medical instruments, human tissues, implants, of specimens, etc. Mouth rim 44, is a feature of container 33, intended for only serious airborne microorganism or level 5 Biohazards. Mouth rim 44, can be designed to be inflated by an additional port hole,. It can be designed to have absorbent fibers that can be prechemically treated with any Effective disinfectant that is disease or organism specific, when the mouth rim is inflated. Mouth rim 44, must be tested to see what design will work best with what organism, And or if its effectiveness warrants the additional costs.

The foregoing discussion discloses and describes merely exemplary embodiments of The present invention. One skilled in the art will readily recognize from such discussion, And from the accompanying drawings and claims, that various changes, modifications And variations can be made therein without departing from the spirit and scope of the Invention as defined in the following claims.

I claim:

1. A storage container for isolation and containment of medical instruments, devices and biohazard waste comprising an elongated tubular storage container made of puncture resistant, gas autoclavable material, said storage container including a closed lower end and an open upper end, said storage container having a plastic twist off lid attachable to the open upper end and including a string connected between the lid and container to attach the lid to the container, said lid further including a biohazard waste symbol thereon, said elongated container including a port hole of entry connected thereto near the open upper end, said port hole of entry comprising a second container section of smaller cross section than the cross section of the storage container and connected thereto in sealed fashion to allow entry of solution or chemicals to the container without opening the lid on the container upper end, said port hole of entry including therein a semi permeable membrane between the port hole of entry and the main body of the storage container, said semi permeable membrane material allowing entry of fluid without leakage thereafter, said storage container having a mouth rim to block and prevent a back splash of airborne microorganism from the container, said mouth rim being made of rubber or plastic pretreated chemically with a disinfectant, said storage container further including a dry chemical formula as a disinfectant at the closed lower end thereof.

2. The storage container of claim 1 wherein said dry chemical is dry formula bleach.

3. The storage container of claim 1 wherein an effervescence agent and/or detergent is included in the dry chemical formula.

4. The storage container of claim 1 wherein said mouth rim is irrigable or inflatable through an additional port hole of entry.

5. The storage container of claim 4 wherein the mouth rim includes absorbent fiber material to hold disinfectant and keep it moist.

6. The storage container of claim 1 wherein a magnet is bonded to the bottom of the storage container to help stabilize the container.

7. The storage container of claim 1 further including a base container for holding the storage container securely.

* * * * *